United States Patent
Hearn et al.

(10) Patent No.: US 9,693,584 B2
(45) Date of Patent: *Jul. 4, 2017

(54) SIMULATED CIGARETTE DEVICE

(75) Inventors: Alex Hearn, London (GB); Moritz Bolle, London (GB)

(73) Assignee: Kind Consumer Limited, London (GB)

( * ) Notice: Subject to any disclaimer, the term of this patent is extended or adjusted under 35 U.S.C. 154(b) by 1509 days.

This patent is subject to a terminal disclaimer.

(21) Appl. No.: 13/141,972

(22) PCT Filed: Dec. 23, 2009

(86) PCT No.: PCT/GB2009/002961
§ 371 (c)(1),
(2), (4) Date: Sep. 9, 2011

(87) PCT Pub. No.: WO2010/073018
PCT Pub. Date: Jul. 1, 2010

(65) Prior Publication Data
US 2011/0315152 A1 Dec. 29, 2011

(30) Foreign Application Priority Data
Dec. 23, 2008 (GB) .................................. 0823491.6

(51) Int. Cl.
*A24F 47/00* (2006.01)
*A61M 15/00* (2006.01)
(Continued)

(52) U.S. Cl.
CPC ....... *A24F 47/002* (2013.01); *A61M 15/0091* (2013.01); *A61M 15/0093* (2014.02); *A61M 15/06* (2013.01); *A61M 16/20* (2013.01)

(58) Field of Classification Search
None
See application file for complete search history.

(56) References Cited

U.S. PATENT DOCUMENTS 3,721,240 A * 3/1973 Tamburri ................. 128/202.21
4,171,000 A 10/1979 Uhle
(Continued)

FOREIGN PATENT DOCUMENTS

DE 4030257 A1 4/1992
DE 10051792 A1 * 5/2002
(Continued)

OTHER PUBLICATIONS

International Search Report for Application No. PCT/GB2009/002961 dated Apr. 6, 2010.
(Continued)

*Primary Examiner* — Phu Nguyen
(74) *Attorney, Agent, or Firm* — Patterson & Sheridan, L.L.P.

(57) ABSTRACT

A simulated cigarette device with a substantially cylindrical cigarette-like shape comprising a reservoir of a pressurized composition including an inhalable substance and a propellant. A refill valve is in communication with the reservoir via which the reservoir is refilled. A breath-activated valve selectively controls the flow through a reservoir outlet and hence through an inhaling outlet in the device. The size of the reservoir, the pressure within the reservoir and the size of the reservoir outlet at its narrowest point are arranged so that, when the breath-activated valve is fully opened, the reservoir will discharge in less than 30 seconds.

21 Claims, 7 Drawing Sheets

(51) Int. Cl.
*A61M 15/06* (2006.01)
*A61M 16/20* (2006.01)

(56) References Cited

U.S. PATENT DOCUMENTS

| | | | |
|---|---|---|---|
| 5,535,735 | A | 7/1996 | McPherson |
| 6,016,801 | A | 1/2000 | Philips |
| 6,889,687 | B1 * | 5/2005 | Olsson ..................... 128/200.14 |
| 2006/0018840 | A1 * | 1/2006 | Lechuga-Ballesteros et al. .............................. 424/45 |
| 2013/0213420 | A1 | 8/2013 | Hon |

FOREIGN PATENT DOCUMENTS

| | | |
|---|---|---|
| EP | 1618803 A1 | 1/2006 |
| FR | 2665639 A1 | 2/1992 |
| WO | 97/12639 A1 | 4/1997 |
| WO | 2009001078 A2 | 12/2008 |
| WO | 2009001082 A1 | 12/2008 |

OTHER PUBLICATIONS

United Kingdom Search Report for Application No. 0823491.6 dated Apr. 23, 2009.
Canadian Office Action dated Nov. 17, 2015, for Canadian Patent Application No. 2,747,901.

* cited by examiner

SIMULATED CIGARETTE DEVICE

The present invention relates to a simulated cigarette device.

The risks of smoking are widely known and, as a result of these, a variety of nicotine replacement therapies (NRTs) are available. These include the nicotine patch, gum, tablet and lozenge. Although these have met with some success, they suffer from two important drawbacks. Firstly, they make no attempt to replicate the physical act of smoking which is an important part of the smoking experience. Secondly, a cigarette produces a sharp pharmacokinetic spike in nicotine plasma concentration in the blood which is responsible for the "hit" that is craved by a smoker. With the tobacco cigarette, the concentration of nicotine in the arterial blood plasma is carried across the blood brain barrier via the carotid arteries within 10 seconds of inhalation. The average smoker self-titrates his nicotine level via inhalation until he perceives he has gained the adequate nicotine concentration that will satiate his craving. Such a system relies on the smoker being able to access a consistent dose of nicotine upon every inhalation. Correspondingly, nicotine replacement therapies (NRT) such as patch, gum and lozenge are slower in uptake and because they create a gradual build-up of nicotine over time, and hence are unsatisfactory to many smokers. With conventional NRT, the method has been to provide a consistent baseline dose of nicotine in the venous blood plasma, such as will reduce the craving 'spikes' of pharmacologically active nicotine. This has had mixed success with the quick rate of smokers undergoing these devices along less than 3% (UK, Royal College of Physicians, 2006). As such, there is a growing call in line with governmental harm reduction policies around the world, to encourage faster acting devices such as inhalers and nasal sprays that may do better to satiate the craving spike of a smoker. Nasal sprays have been shown to provide quick update, however the delivery is often unpleasant and users often find it socially awkward to administer several times a day. Currently available inhalators are more popular in this regard. Devices such as the Nicorette® Inhalator provide an inhalation of volatile evapourated nicotine which upon puffing, delivers its dose primarily through the buccal system (i.e. the mouth). Less than 5% of the vapour enters the respiratory system. As such, although for the user, it is a more acceptable delivery format, the nicotine must cross the mucosal membranes in the lining of the oral cavity, and so the rate of pharmacokinetic update is similar in speed to gum. This has found poor acceptance with the user since he does not experience a satiation of the craving spike in the timeframe that is desired.

In an attempt to replicate the physical act of smoking, a number of simulated cigarette devices have been proposed in the art. These include, for example, U.S. Pat. No. 3,721,240, U.S. Pat. No. 3,631,856, U.S. Pat. No. 4,393,884, DE 2 442 774, DE 2 653 133 and DE 4 030 257, as well as electronic devices such as EP 1618803, and portable delivery systems such as U.S. Pat. No. 6,016,801.

Of note amongst these is DE 4 030 257. This physically resembles a cigarette. It has a reservoir of material to be dispensed which may be refillable. Alternatively, the device is disposable. Dispensing is triggered either by a user sucking on the device to open a valve, or by a manually operable valve. The document does not address the dosage regime and, as far as we are aware, no commercial product to this design has been produced.

In fact, numerous attempts to produce a simulated cigarette device, as far as we know, the only one which has met with any commercial success is the Electronic Cigarette™. This comprises a mouth piece which contains a rechargeable battery, control circuitry and an atomiser to generate a vapour for inhalation. A refill cartridge containing the material to be vaporised is screwed into the mouth piece. The device replicates certain aspects of the smoking experience by providing a glowing tip and generating a visible vapour that the user may exhale. Despite this, the device has a number of drawbacks.

The battery in the mouthpiece requires periodic re-charging. This is inconvenient for a user who, if they want to use the device for an extended period, must remember to charge the device before use, or have the inconvenience of taking the charger with them and then finding somewhere to plug it in.

Figure 9:
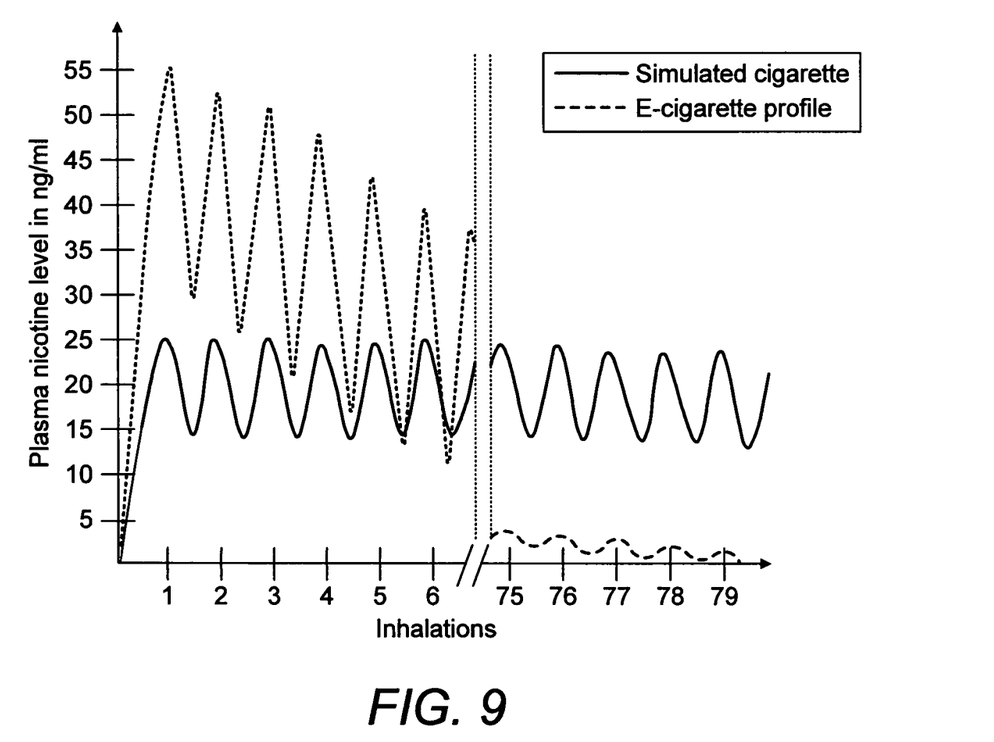
FIG. 9 is a graph showing the dosage regime as compared to the discharge regime from the Electronic Cigarette™.

The biggest drawback of the device is the dispensing regime. Each refill contains the same amount of nicotine as around 20 cigarettes. This is done in order to provide maximum convenience to the user. However, this also results in a number of drawbacks. The user may simply use the device uninterrupted, often paying little attention to what they are doing, so that they may continue to inhale nicotine equivalent to a reasonably large number of cigarettes without really being aware of this. Further, because of the size of the reservoir of nicotine and the manner in which it is dispensed, the amount of nicotine dispensed during each inhalation varies enormously. This is shown by the broken line FIG. 9 which shows the plasma nicotine level that a user experiences following each inhalation. Tests have shown that, when new, the device will delivery 0.5 mg of nicotine per standard inhalation down to 0.003 mg nicotine when the refill is almost used up. In the early stages, therefore, the electronic cigarette is delivering more than twice the peak amount of nicotine of a tobacco cigarette, but close to end of the lifetime of the refill will deliver only a few percent of the nicotine level of a tobacco cigarette.

This highly inconsistent dose is unsatisfactory as a user's physiological responses can fluctuate significantly according to how many inhalations are left in the refill cartridge. Many users are likely to find this highly unsatisfactory.

According to the present invention, there is provided a simulated cigarette device with a substantially cylindrical cigarette-like shape comprising a reservoir of a pressurised composition including an inhalable substance and a propellant, a refill valve in communication with the reservoir via which the reservoir is refilled, a breath-activated valve to selectively control the flow through a reservoir outlet and hence through an inhaling outlet in the device, wherein the size of the reservoir, the pressure within the reservoir and the size of the reservoir outlet at its narrowest point are arranged so that, when the breath-activated valve is fully opened, the reservoir will discharge in less than 30 seconds.

The present invention overcomes the above mentioned drawbacks of the electronic cigarette. Rather than trying to cram as high a dosage as possible into the reservoir, the present invention takes the opposite approach by providing a reservoir each will last for approximately the same duration as a normal cigarette. At the end of this time, the reservoir must be refilled.

This means that the user cannot continue to obtain more nicotine than they would derive from a single cigarette without having to pause to refill the device. This will make them more conscious of the amount that they are actually inhaling and will stop them from accidentally inhaling far more than intended. This action also replicates the normal smoking action of returning to the cigarette pack to extract a fresh cigarette.

More importantly, the small reservoir in combination with the presence of a propellant ensures that the peak flow upon each inhalation remains highly consistent. This is shown by the solid line in FIG. 9.

As the discharge of the inhalable substance is driven by the propellant, it does not require a battery and the inconvenience of recharging is eliminated.

Preferably, the reservoir has a volume of 500-5000 mm$^3$ and more preferably be 750-1500 mm$^3$. The pressure is preferably between 200-5,000 kPa and more preferably between 300-600 kPa. The outlet is preferably from 0.1-1 mm in diameter and more preferably 0.1-0.3 mm in diameter at its narrowest point. It should be borne in mind, however, that the three parameters are closely linked, such that a small high pressure reservoir would require only a small outlet to discharge within the required time and, conversely, a large low pressure reservoir would require a larger orifice.

The propellant is preferably HFA134a (1,1,1,2-Tetrafluoroethane, a high vapour-pressure substance, which when released sends the liquid propellant at a relatively high speed from the canister. When the nicotine solution, preferably with a mixture of co-solvents propylene glycol, polyethylene glycol and ethanol is dissolved in the propellant, it is released in an aerosol in relation to the volume of propellant exiting via the orifice, thus a uniform dose of nicotine is released in proportion to the propellant vapourising. The nicotine is preferably mixed in a low ratio to the propellant between 0.1-10%, preferably 3-6%%% in relation to total fill weight of propellant. Additionally HFA227 (1,1,2,3,3,3-heptafluoropropane) or 152a (1,1-Difluoroethane) could be used. The ratio of co-solvent to nicotine, whether free base, derivative or salt, will be between 0.01% and 2%, and preferably between 1% and 1.5% to ensure appropriate uniform distribution of nicotine in the solution.

As the manner in which a user will suck on the device will vary, there is no direct correlation between the time to discharge the reservoir and the number of inhalations that it will provide before requiring a refill. The average mean inhalation for a user is around 1.2 seconds, so that the reservoir provides up to 30 inhalations before requiring a refill. Preferably, the reservoir will discharge in less than 25 seconds and more preferably less than 20 seconds. This will result in a device which can provide correspondingly fewer inhalations.

In order to achieve a consistent discharge flow rate, the size of the reservoir, the pressure within the reservoir and the size of the reservoir outlet at its narrowest point are preferably arranged so that the peak volumetric flow rate of inhalable composition for each discharge with the breath-activated valve fully open has a variation of less than 10% and more preferably less than 5% as the reservoir is discharged. In other words, the peak inhalable composition that a user draws from the device will vary by less than 10% and preferably less than 5% from a fully refilled reservoir to a nearly empty reservoir. That is not to say that the user will receive a fixed amount of inhalable composition for each inhalation as this will be dependent upon the duration of the inhalation. However, the consistency of the peak volumetric flow rate means that the user is able to reliably regulate this amount for themselves much as they do with a tobacco cigarette by inhaling for longer if they wish to inhale a greater quantity of the inhalable composition.

The present invention preferably also extends to a system comprising a device according to the present invention in combination with a refill device. The refill device preferably has a substantially cuboid housing with a cigarette pack-like shape containing the pressurised composition as a refill for the simulated cigarette device and has means for selectively retaining the simulated cigarette. This mimics the look and feel of the cigarette and cigarette pack.

Preferably the height is 44 to 176 mm, but most preferably 88 mm, with a width 21 mm to 112 mm but most preferably 56 mm, and the depth 8 mm to 60 mm but most preferably 24 mm. This corresponds most preferably to the average size of a 20-pack of tobacco cigarettes and conforms with existing shelving and vending formats.

The refill device preferably contains a canister than can provide 20 refills to a simulated cigarette device. For the most preferable format, said canister cannot be more than 80 mm in height, or 23 mm in depth. Most preferably the canister has an outer diameter of 22.5 mm, with an inner diameter of 21.9 mm with a canister length of 60 mm.

Factoring in 20% ullage, an actual fill volume of 18,081 mm$^3$ of formulation can be retained in the refill cannister. In order to deliver 20 fills per simulated cigarette device, considering an outer diameter of 8 mm which corresponds to the outer diameter of a tobacco cigarette, and considering an inner diameter of 6 mm, the total fill length of the device reservoir is 31.9 mm with an area of 28.8 mm that corresponds to a 0.9 ml fill By establishing an even pressure of between 3-20 bar, most preferably 5-6 bar in the refill canister with the propellant at 95% weight of total solution, this can be translated via pressure differential during the transfill, to equalise at the same pressure in the device reservoir. Establishing such a pressure can modify the performance of the device in terms of its flow rate and dosing delivery. It is advantageous to have the propellant level between 60% and 99% of the total formulation solution, most preferably between 95% and 99% in order to achieve flow rates most acceptable to a user.

Thus in order to achieve a requirement that is the same in terms of capacity of delivery as a tobacco cigarette, where the average length of puff is 1.2 seconds, the combination of the reservoir fill, the size of the outlet valve on the device and the ratio and pressure of the propellant, can achieve consistent and uniform doses of nicotine in aerosol, whereby the device can deliver 12-15 puffs per fill, and that the discharge flow rate from the simulated cigarette device with the valve fully opened can be consistently maintained between 30 and 300 mm$^3$/sec, preferably between 60 and 100 mm$^3$, most preferably 63 mm$^3$/sec whereby the dose of nicotine per puff is then maintained at 75 mm$^3$ of solution, giving an even and consistent dosing each puff. This delivers an even dosing stream of nicotine akin to a tobacco cigarette, at a similar dose per puff and flow rate of a medium strength tobacco cigarette, as well as providing the same capacity for dose delivery as a conventional 20 pack of tobacco.

The refill device preferably further comprises a dose counter to register the number of times that the simulated cigarette device is refilled and display this to a user.

The refill device preferably has a means for retaining the simulated cigarette device in a position which is different from the position in which the simulated cigarette device is refilled.

The refill device preferably has a housing containing the pressurised composition for the simulated cigarette and having means for selectively retaining the simulated cigarette device entirely within the housing.

An example of a device and system in accordance with the present invention will now be described with reference to the accompanying drawings, in which.

The general structure of the simulated cigarette device is disclosed in our own earlier WO 2009/001082. The details of the refill pack are provided in WO 2009/001078 and details of a formulation are given in WO 2009/001085.

Figure 4:
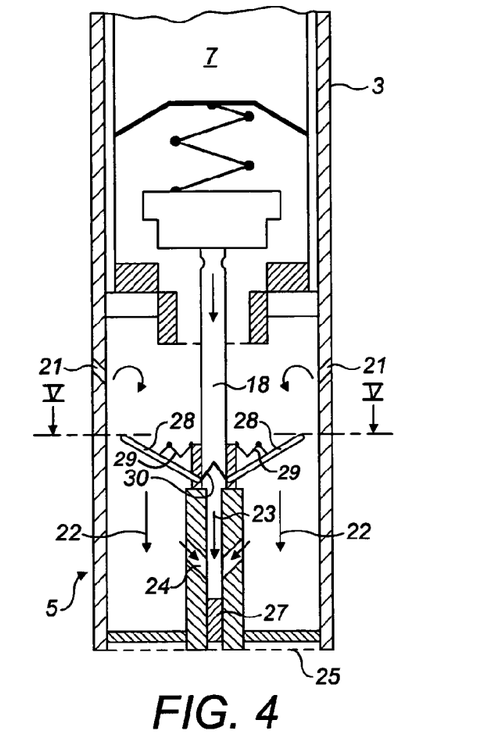
FIG. 4 is a view similar to FIG. 3 showing an alternative design of the breath activated valve.
Figure 5:
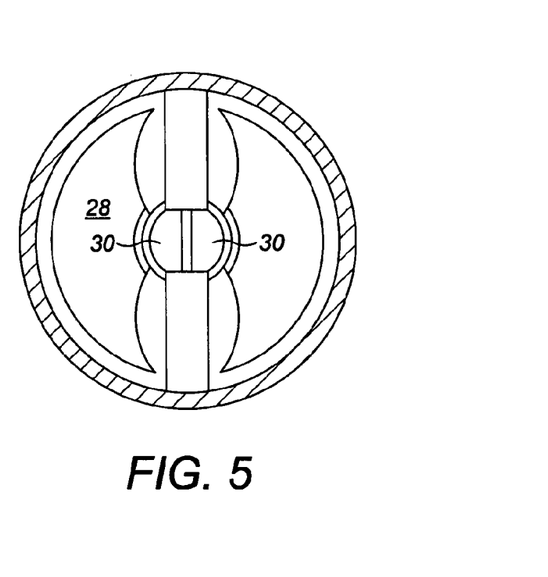
FIG. 5 is a cross-section through line V-V in FIG. 4.
Figure 6:
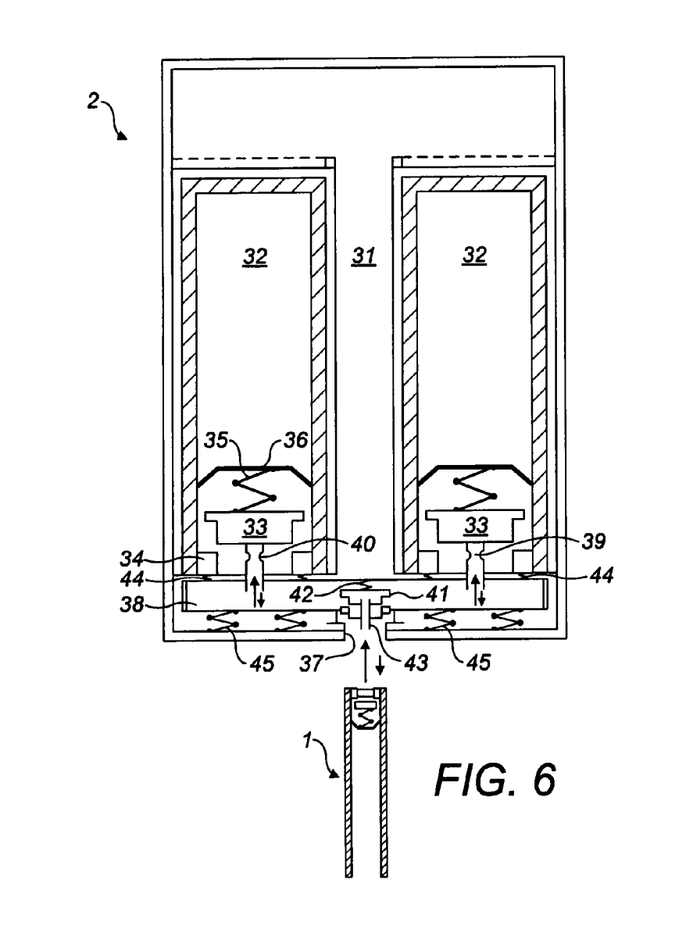
FIG. 6 is a schematic cross-section of a refill unit.
Figure 7:
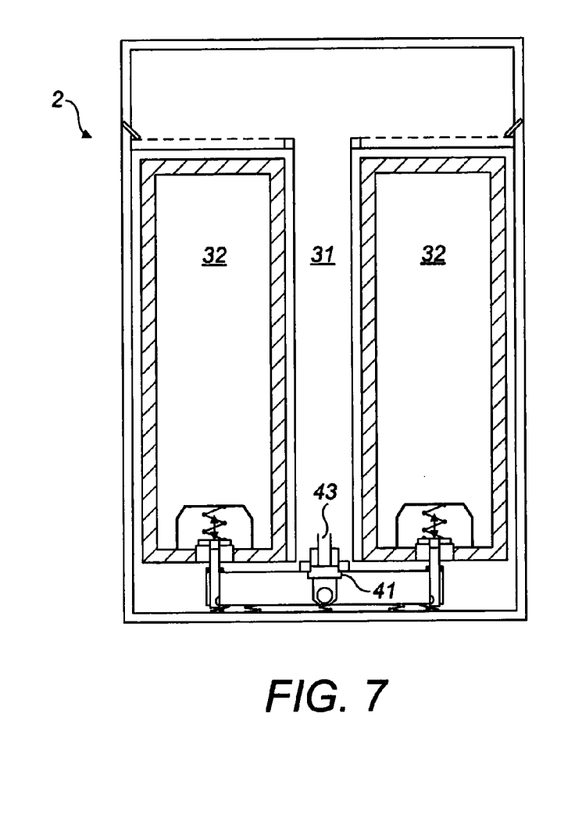
FIG. 7 is a schematic view similar to FIG. 6 of a second refill unit.
Figure 8:
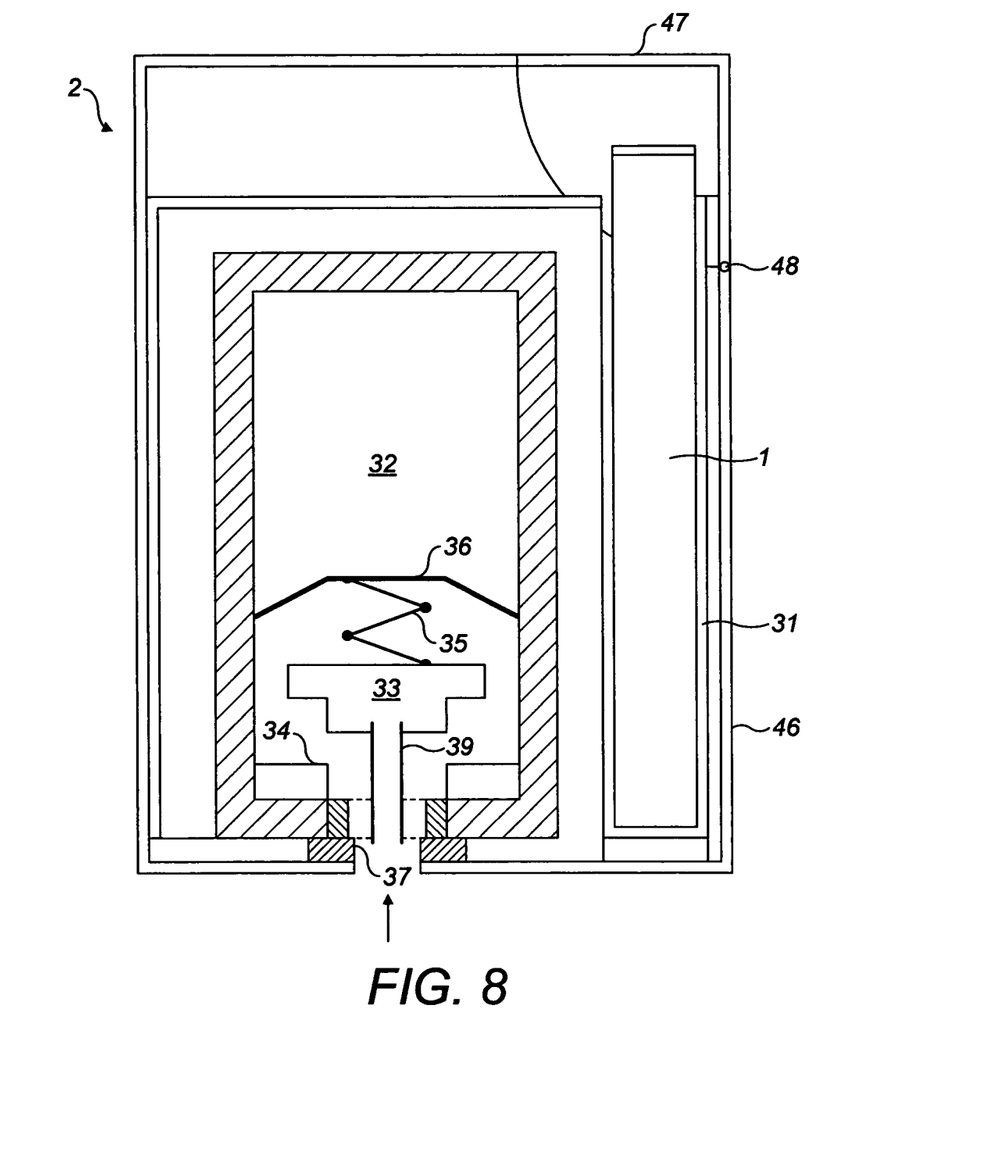
FIG. 8 is a schematic cross-section showing a third refill unit.

The system comprises two main components namely a simulated cigarette device 1 shown in FIGS. 1 to 5 and a refill unit 2 shown in FIGS. 6 to 8.

Figures 1, 2A, 2B:
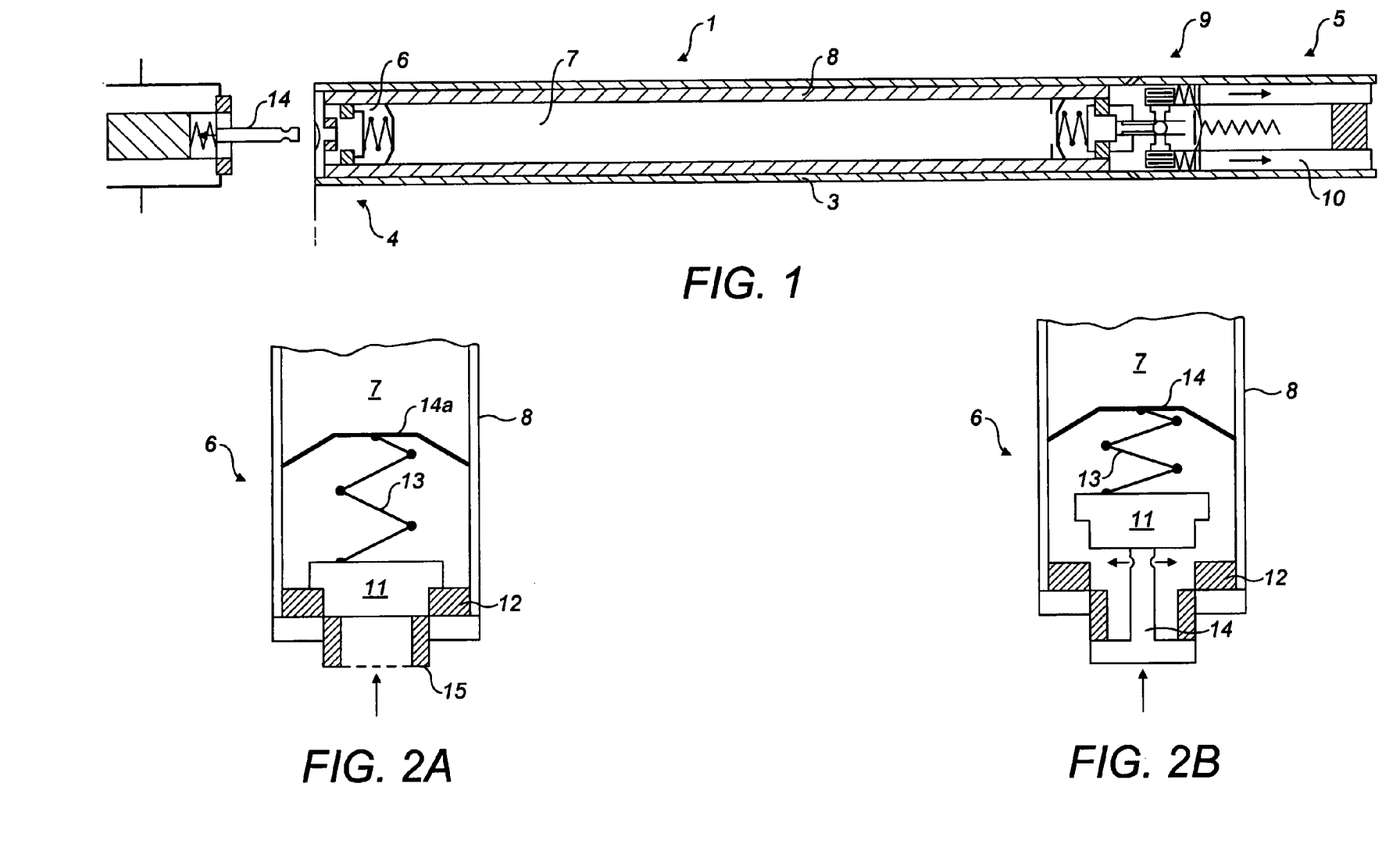
FIG. 1 is a schematic cross-section through the device also showing the refill nozzle.
FIG. 2A is a schematic cross-section through a distal end of the device with a refill valve in the closed position.
FIG. 2B is a view similar to FIG. 2a with the valve in the open position.

The simulated cigarette device 1 will be described first. This comprises an elongate hollow cylindrical housing 3. One end of this housing is a refill end 4 and the opposite end is an inhaling end 5. At the refill end a check valve 6 is described in more detail below. This leads to a reservoir 7 which extends along a substantial portion of the length of the device. As shown in FIG. 1, the reservoir is defined by a cylindrical sleeve 8 tightly fitted within the cylindrical housing 3. It could, however, be defined by the cylindrical housing 3 itself. At the opposite end of the reservoir 7 to the refill end 4 some three quarters of the way along the device is a breath activated outlet valve 9 that is described in more detail below. This leads to an outlet at the inhaling end 5. The reservoir 7 is periodically filled with solution through the check valve 6. A user then sucks on the inhaling end 5 periodically opening the breath activated valve 9 to draw doses of the solution from the reservoir 7.

The check valve 6 will now be described in more detail with reference to FIGS. 2A and 2B. The check valve comprises a valve element 11 which is biased onto a valve seat 12 by a spring 13. The spring 13 is supported at its opposite end by a spring support 14a which is open to allow solution to pass. The refill end 4 also has a refill seat 15 upstream of the valve element 11. In order to refill the reservoir, a refill nozzle 14 is inserted into the refill end 4 of the device 1. The refill nozzle 14 pushes on valve 11 to lift it from its seat, while the end of the nozzle seals against nozzle seat 15 to seal the end of the reservoir during the refill processes. As shown in FIG. 1, the refill nozzle 14 is spring-loaded such that it automatically dispenses solution when pressed against the valve element 11. Alternatively, an independent release mechanism may be provided for the refill.

As the nozzle is withdrawn, the spring 13 pushes the valve element back onto its seat to seal the end of the reservoir.

The breath activated valve 9 will now be described with reference to FIG. 3. This comprises a valve element 16 in the form of an elongate rod with a through hole 17. This through hole 17 is positioned in a tubular outlet 18 leading to the reservoir 7. In the position shown in FIG. 3, the through hole 17 is perpendicular to the tubular outlet 18 thereby blocking flow through the tubular outlet 18. When the valve element 16 is rotated through 90° the through hole 17 comes into alignment with the tubular outlet 18 allowing flow from the reservoir 7.

Figure 3:
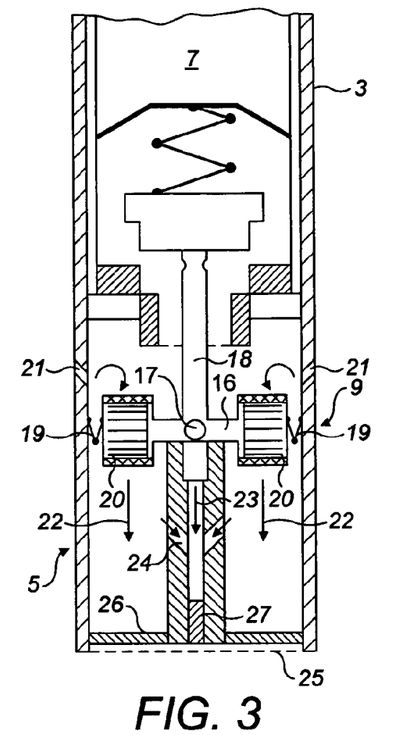
FIG. 3 is a schematic cross-section showing the breath activated valve at the proximal end.

The valve element 16 is held in the closed position shown in FIG. 3 by a pair of biasing springs 19. At either end of the valve element 16 is a vane system 20. Upstream of the vane system 20 are a pair of oblique inlets 21. These are positioned and oriented such that air flowing through the inlet impinges on the vane system 20 in such a way as to cause the valve element to rotate to the open position against the action of the biasing springs 19, thereby opening the valve. Thus, the valve is activated by a user sucking on the inhaling end of the device. When the sucking stops, the biasing springs 19 cause the valve to close.

As can be seen in FIG. 3, there are two streams flowing towards the inhaling end 5. These are the ambient air stream from the oblique inlets 21 designated by arrows 22 and the stream from the reservoir 7 which has passed through through hole 17 as designated by reference numeral 23, a pair of bleed flow orifices 24 bleed a proportion of the ambient air stream 22 into the stream 23 and are directed obliquely so as to promote flow towards the inhaling end 5. This is done as the gas from the reservoir may be cold and it is therefore diluted by the ambient air from streams 20, as well as provide greater volumetric inhalation. At the inhaling end is a screen 25 which holds in place an annular filter element 26 for the external flow passageway and a central filter element 27 for the flow from the reservoir. These prevent external debris from entering the device.

An alternative arrangement of breath activated valve will now be described with reference to FIGS. 4 and 5.

Most components of the inhaling end 5 are the same as those described previously and have been designated with the same reference numerals. Only the valve mechanism itself is different. This comprises a pair of plates 28 which are pivotally mounted and biased into the first position shown in FIG. 4 by a respective balancing spring 29. Extending generally perpendicular from each plate 28 are sealing elements 30. The sealing elements 30 are preferably made of a material with a degree of resilience such as an elastomer, or may be a rigid material with a resilient tip at the end to provide a seal. The seal element meets in the middle of the tubular outlet 18 to seal the flow path through the outlet. In the device, air from oblique inlets 21 impinges on plates 28 causing the plates to rotate downwardly from the position shown in FIG. 4 thereby parting the sealing elements 30 and allowing flow from the reservoir 7. When the suction stops, the plates 28 are urged back to the starting position shown in FIG. 4 and the tubular outlet 18 is sealed again.

A first example of the refill unit will now be described with reference to FIG. 6.

The refill unit is approximately the same size as a cigarette packet and is provided a recess 31 in which the cigarette device 1 can be stored when not in use. The refill unit comprises a pair of cylinders 32 positioned on either side of the recess 31.

Each cylinder 32 has the same construction. Each cylinder has an inlet/outlet valve comprising a valve element 33 which is biased onto a valve seat 34 by biasing spring 35 which is supported on spring support 36.

In order to fill the cigarette device 1 from the refill unit 2, and in order to refill the refill unit 2 itself, a ducting system is provided to provide a flow communication between an inlet/outlet 37 and the cylinders 32. This takes the form of a spring-loaded duct 38 which leads from the inlet/outlet 37 to the two cylinders 32. The duct is provided with a pair of nozzles 39 each of which is arranged to press against a respective valve element 33, and each of which is provided with a plurality of orifices 40 which allow flow communication between the internal space of the cylinder 32 and the spring loaded duct 38. Adjacent to the inlet/outlet 37 is a duct valve 41 normally biased into a closed position by spring 42. A duct nozzle 43 similar to the nozzle 39 is associated with valve 41.

In an unused configuration, the spring-loaded duct 38 is biased into a position closely adjacent to the bottom of the refill unit by a spring 44. At this time, the valve elements 33 are seated as is duct valve 41, each being biased into its closed position by a respective spring. When the cigarette device 1 is inserted in the inlet/outlet 37, the check valve 6 on the cigarette device 1 is opened as described above. The duct valve 41 is pushed into an open position, and the entire spring-loaded duct 38 is lifted to the position shown in FIG. 6 assisted by springs 45. This causes nozzle 37 to lift valve elements 33 from their seats. There is now flow communication from the cylinders 32 into the reservoir 7 of the cigarette device. As the cylinders 32 are at the higher pressure than the cigarette device, the air flows into the reservoir 7. Each cylinder 32 is at has a sufficient solution to refill the cigarette device 14 times.

Additionally the refill unit, preferably containing an inhalable composition with oxygen, can be manually pumped by a compression pump activated by a trigger or push-down button located on the top or the side refill pack much like the manual habit associated with a cigarette lighter. This serves to prime, regulate and re-pressurize the refill unit so a constant dose and pressure is maintained and delivered.

When the cylinders 32 run low, they themselves are refillable. This is done using the same mechanism as is used to refill the cigarette device from the cylinders. In order to do this, a high pressure source (not shown) is placed into the inlet/outlet 37 in the same way that the cigarette device is inserted and the same flow path is opened up. As the high pressure source is at a higher pressure than the cylinders 32, the cylinders are refilled.

It is envisaged, for example, that the high pressure source may be provided as a vending machine such that the user may refill their cylinder from this, or may be a canister that a user keeps in their house or car.

FIG. 7 shows a second refill unit 2. This is similar to the first unit, but, in this case, is designed to refill the cigarette device when the cigarette device is in the recess 31. Thus, the duct valve 41 and duct nozzle 43 are inverted from their positions from FIG. 6 and corresponding adjustments are made to the rest of the mechanism.

A third refill unit is shown in FIG. 8. This unit comprises a casing 46 having a lid 47 which is hinged at hinge 48. When the lid is opened, the cigarette device 1 may be inserted into and removed from recess 31. The refill comprises a single cylinder 32 constructed in accordance with the cylinders described in relation to FIG. 6. As this example only has a single cylinder, the inlet/outlet 37 directly below the nozzle 39 such that the cigarette device 1 and high pressure source press directly on the valve element 33.

Figure 10:
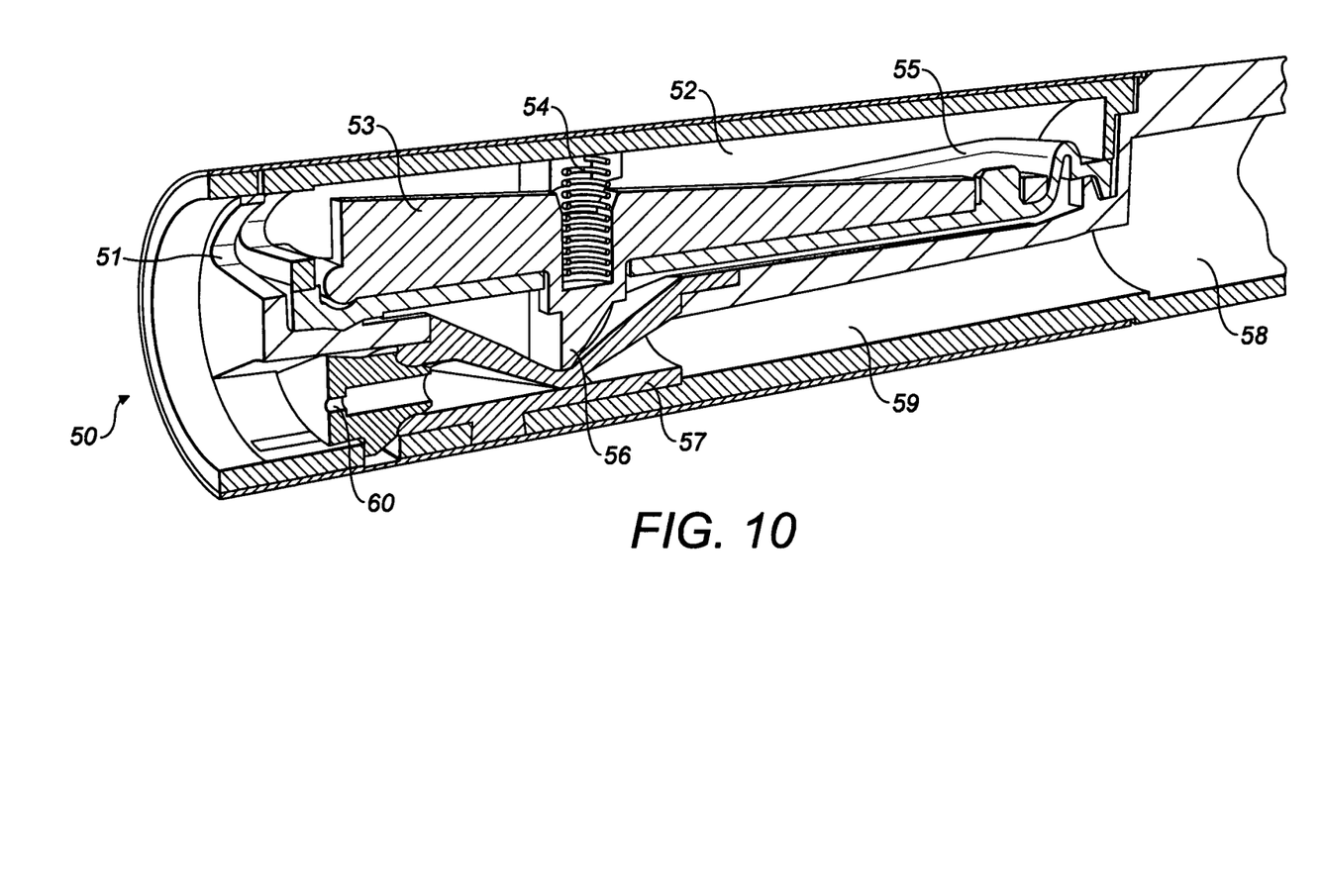
FIG. 10 is a cut away perspective of the inhalation end of a cigarette device with a further example of a breath-activated valve in a closed position.
Figure 11:
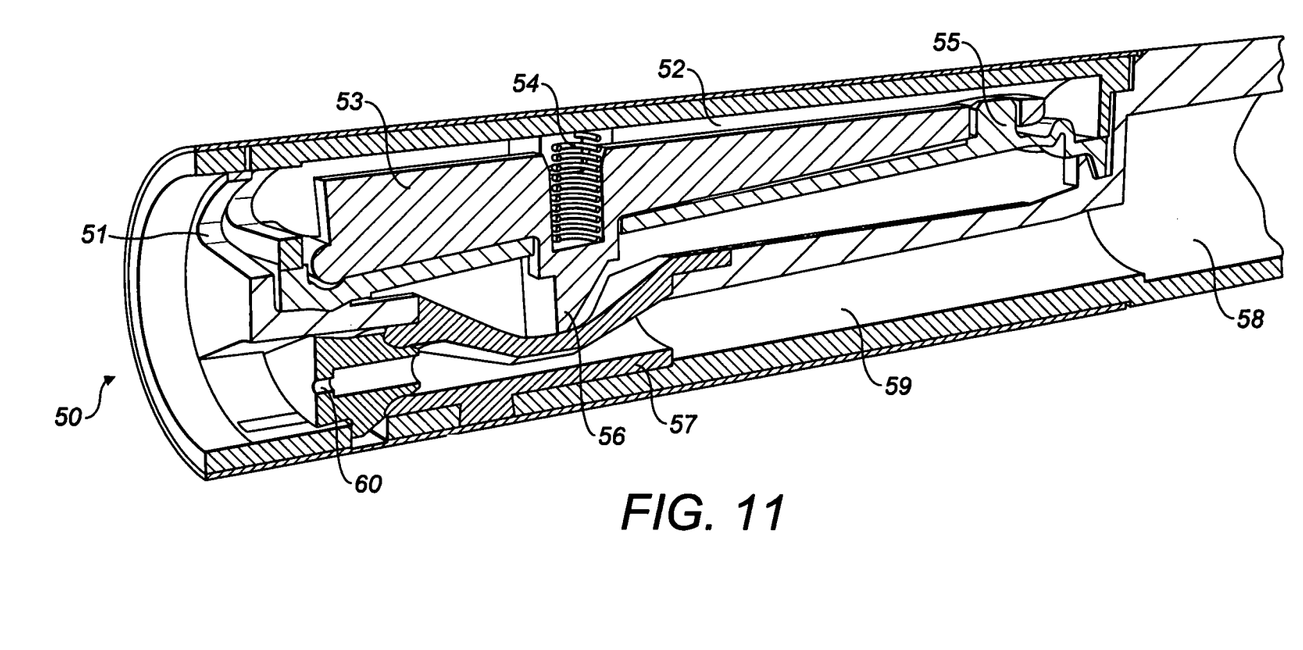
FIG. 11 is a view similar to FIG. 10 showing the valve open.

A further arrangement of breath-activated valve is shown in FIGS. 10 and 11.

When a user sucks on the outlet end 50 with the device in the configuration shown in FIG. 10, the suction is communicated by a suction orifice 51 to a chamber 52 thereby lowering the pressure in this chamber. This causes a pivotally mounted vane 53 to be lifted against the action of a spring 54 to the position shown in FIG. 2 deforming a diaphragm 55 into the configuration shown in FIG. 2 and lifting a jaw 56 to allow a deformable tube 57 to open, thereby allowing the inhalable composition from a reservoir 58 along an outlet path 59 through the deformable tube 57 and out through an outlet orifice 60. The degree of suction applied by the user will determine the extent to which the vane 53 moves and therefore the amount of composition that the user receives. As soon as a user stops sucking, atmospheric pressure will return to the chamber 52 via the suction orifice 51 and the spring 54 will return the vane to the FIG. 1 position thereby pinching the tube 57 closed.

The invention claimed is:

1. A simulated cigarette device with a substantially cylindrical cigarette-like shape comprising a reservoir of a pressurised composition including an inhalable substance and a propellant, a refill valve in communication with the reservoir via which the reservoir is refilled from a refill unit which is external to the simulated cigarette device, a breath-activated valve to selectively control a flow of the inhalable substance and the propellant through a reservoir outlet and hence through an inhaling outlet in the device, wherein a size of the reservoir, a pressure within the reservoir and a size of the reservoir outlet at its narrowest point are arranged so that, when the breath-activated valve is fully opened, the reservoir will discharge in less than 30 seconds.

2. A device according to claim 1, wherein the reservoir has a volume of 500-5000 mm$^3$.

3. A device according to claim 2, wherein the reservoir has a volume of 750-1500 mm$^3$.

4. A device according to claim 1, wherein the pressure is between 200-5000 kPa.

5. A device according to claim 4, wherein the pressure is between 300-600 kPa.

6. A device according to claim 1, wherein the outlet is from 0.1-1 mm in diameter at its narrowest point.

7. A device according to claim 6, wherein the outlet is from 0.1-0.3 mm in diameter at its narrowest point.

8. A device according to claim 1, wherein the propellant is selected from HFA134a, HFA227 and HFA152a.

9. A device according to claim 1, wherein nicotine is present at a weight of 0.1 to 10% of the weight of propellant.

10. A device according to claim 9, wherein nicotine is present at a weight of 3 to 6% of the weight of propellant.

11. A device according to claim 1, wherein the reservoir will discharge in less than 25 seconds.

12. A device according to claim 11, wherein the reservoir will discharge in less than 20 seconds.

13. A device according to claim 1, wherein the size of the reservoir, the pressure within the reservoir and the size of the reservoir outlet at its narrowest point are preferably arranged so that the peak volumetric flow rate of inhalable composition for each discharge with the breath-activated valve fully open has a variation of less than 10%.

14. A device according to claim 13, wherein the size of the reservoir, the pressure within the reservoir and the size of the reservoir outlet at its narrowest point are preferably arranged so that the peak volumetric flow rate of inhalable composition for each discharge with the breath-activated valve fully open has a variation of less than 5%.

15. A device according to claim 1, wherein the device has a discharge flow rate of from 30 to 300 m$^3$/s and preferably from 60 to 100 m$^3$/s.

16. A device according to claim 1, wherein the propellant level is between 60% and 99%, and preferably between 95% and 99% by weight, of the total formulation solution.

17. A system comprising a device according to claim 1, in combination with a refill device.

18. A system according to claim 17, wherein the refill device has a substantially cuboid housing with a cigarette pack-like shape containing the pressurised composition as a refill for the simulated cigarette device and has a recess for selectively retaining the simulated cigarette.

19. A system according to claim 17, wherein the refill device further comprises a dose counter to register the number of times that the simulated cigarette device is refilled and display this to a user.

20. A system according to claim 17, wherein the refill device has the recess for retaining the simulated cigarette device in a position which is different from the position in which the simulated cigarette device is refilled.

21. A system according to claim 17, wherein the refill device has a housing containing the pressurised composition for the simulated cigarette and having the recess for selectively retaining the simulated cigarette device entirely within the housing.

* * * * *